United States Patent
Koblanski

[19]

[11] Patent Number: 5,865,759
[45] Date of Patent: Feb. 2, 1999

[54] METHOD AND APPARATUS FOR NON-INVASIVE ASSESSMENT OF CARDIAC FUNCTION BY MONITORING ACCELERATION OF THE HEART

[75] Inventor: John Koblanski, Burnaby, Canada

[73] Assignee: Texon Technologies Ltd., Vancouver, Canada

[21] Appl. No.: 834,031

[22] Filed: Apr. 11, 1997

[51] Int. Cl.$^6$ .................................................. A61B 5/00
[52] U.S. Cl. ........................................................ 600/508
[58] Field of Search ................................. 600/500, 501, 600/502, 504, 508

[56] References Cited

U.S. PATENT DOCUMENTS

| | | | |
|---|---|---|---|
| 4,993,420 | 2/1991 | Welkowitz et al. | 600/504 |
| 5,033,472 | 7/1991 | Sato et al. | 600/504 |
| 5,293,874 | 3/1994 | Takahashi et al. | 600/500 |

OTHER PUBLICATIONS

Morton E. Tavel, "Ejection Sound (Ejection Click)" Textbook: Clinical Phonocardiography and External Pulse Recording, Third Edition, 1978 Yearbook Medical Publishing, Inc., pp. 75–78.

Morton E. Tavel, "Normal Sounds and Pulses: Relationships and Intervals Between the Various Events," Textbook: Clinical Phonocardiography and External Pulse Recording, Fourth Edition, 1978 Yearbook Medical Publishing, Inc., pp. 39–45.

Alberto Benchimol, "Ultrasound," Textbook: Non–Invasive Diagnostic Techniques in Cardiology, 1977, The Williams and Wilkins Co., pp. 15–38.

Robert F. Rushmer, Textbook: Cardiovascular Dynamics, 1961, W.B. Saunders Company, pp. 50–52 and 91–97.

Robert F. Rushmer, "Initial Ventricular Impulse A Potential Key to Cardiac Evaluation," Circulation—vol. 29, 1964, pp. 268–283.

*Primary Examiner*—William E. Kamm
*Attorney, Agent, or Firm*—Christie, Parker & Hale, LLP

[57] ABSTRACT

An apparatus and method to assess cardiac function in a human has a sensing mechanism to be positioned on the thyroid cartilage in the neck against the trachea. The sensing mechanism is able to sense a response of the thyroid cartilage to heart function. The apparatus includes a restraining system to hold the sensing mechanism in position. The method of determining cardiac function comprises sensing the response of the thyroid and trachea to heart function.

20 Claims, 4 Drawing Sheets

METHOD AND APPARATUS FOR NON-INVASIVE ASSESSMENT OF CARDIAC FUNCTION BY MONITORING ACCELERATION OF THE HEART

FIELD OF THE INVENTION

This invention relates to an apparatus to assess cardiac function in humans and is of particular value in assessing the risk of heart attack. However the apparatus is also useful in measuring other parameters of cardiac function to determine and locate cardiac and aortic abnormalities.

DESCRIPTION OF RELATED ART

Non-invasive methods of determining cardiac functioning include the following:

a) Mechanical methods that include pulse recording of the jugular, carotid artery or apexcardiogram. This group also include sound recordings, for example the stethoscope and phonocardiographic techniques.

b) Electrical techniques are best exemplified by the electrocardiogram (ECG).

c) Relatively more recent techniques include imaging techniques, for example echocardiography, nuclear cardiography, radiographic techniques and magnetic resonance imaging (MRI).

All of the above the mechanical methods, which rely on vibration and sound recording, involve measuring the movements of the body resulting from cardiac activity. This means that the mass of the body is part of the recording means. This is not desirable. Chest movements, for example, are dependent upon chest shape, and sound recording is dependent upon the amount of fat and the condition of the lung tissue for its amplitude. An accurate trace pattern is difficult to achieve and these techniques are therefore of limited diagnostic value.

Electrical methods measure only the electrical field generated by the heart. This cannot provide a direct measure of the cardiac forces generated by the heart and therefore these methods are incapable of evaluating the heart's function as a pump.

Imaging techniques have limited ability to evaluate the force of the heart's contraction.

Thus none of the above methods is capable of measuring the force of the heart's contraction. As a result the evaluation of the condition of the myocardium is not possible. Heart attack risk cannot be determined by any known non-invasive method. A patient may be diagnosed as normal and yet die of a heart attack shortly after the diagnosis.

Relevant literature includes the following text books, Clinical Phonocardiography and External Pulse recording by Morton E. Tavel, 1978 Yearbook, Medical Publishing Inc.; Non-Invasive Diagnostic Techniques in Cardiology by Alberto Benchimol, 1977, The Williams and Wilkins Co.; and Cardiovascular Dynamics by Robert F. Rushmer, 1961, W.B. Saunders Company.

Rushmer first postulated that acceleration and deceleration of the various structures of the heart and blood explain heart sounds as well as their modifications with changing dynamic conditions. As acceleration is a function of force, the aortic blood acceleration is a manifestation of the force that sets the cardiac structures in motion. Other forces originate from the pressure gradient between the aorta and the left ventricle, which acts over the closed semilunar valve. The valve behaves like a circular, stretched membrane in which the thin, flexible leaflets can be stretched in all directions by the differential aorta—ventricular pressure.

The energy of the rapid ejection phase of the left ventricle expands the aorta and the stored energy is in direct relationship to its wall elasticity. Measurement of the amplitude of the wave created after the maximum ejection rate, is a measure of the elasticity of the wall of the aorta. The elasticity of the aortic valve can also be measured by measuring the amplitude of the wave created after the valve is closed. The most sensitive indicators of performance are the rates of change of momentum as indicated by changes in velocity of the blood and heart mass. This acceleration is directly indicative of myocardial contractility which is one of the most difficult parameters to measure. In 1964 Rushmer established a direct relationship between the initial ventricular impulse and the peak flow acceleration during the systolic ejection—see Circulation—Volume 29: 268–283 1964.

SUMMARY OF THE INVENTION

The present invention seeks to measure the change in momentum as indicated by change in velocity of the blood and heart mass. It enables accurate determination of the acceleration that is directly indicative of myocardial contractility. The present invention records the acceleration of the heart mass and the main blood vessels directly, unlike existing methods which record whole body movement, chest movement or other body parts. These are considered unreliable because of anatomical variations and inertial forces.

In a first aspect the present invention is apparatus to assess cardiac function in a human that comprises:

sensing means to be positioned on the thyroid cartilage in the neck, against the trachea and able to sense the response of the thyroid cartilage to heart function; and means to retain the sensing means in said position.

In a preferred embodiment the sensing means is an accelerometer. The accelerometer may, of course, be used to measure acceleration of the thyroid cartilage and the trachea. The incorporation of an integrating capability, will produce velocity and displacement waveforms of the thyroid cartilage.

In a second aspect the invention also provides apparatus to assess cardiac function in the human, the apparatus comprising:

a mounting strut to extend across the front of the neck of the human;

an accelerometer mounted on said strut to be positionable over the thyroid cartilage in said neck; and mounting means to retain said accelerometer on said neck.

In a preferred embodiment the apparatus has a piezoelectric accelerometer and is in combination with circuitry to produce a waveform characteristic of cardiac function. The waveform can be displayed.

The invention also provide a method of determining cardiac function that comprises sensing the response to the thyroid cartilage and trachea to heart function.

In a further method aspect the invention is a method of determining cardiac function comprising locating sensing means on the neck of a patient, on the patient's thyroid cartilage and against the trachea, with the patient's head inclined forward, and sensing the response to the thyroid cartilage and trachea to heart function.

DESCRIPTION OF PREFERRED EMBODIMENTS

Figure 1:
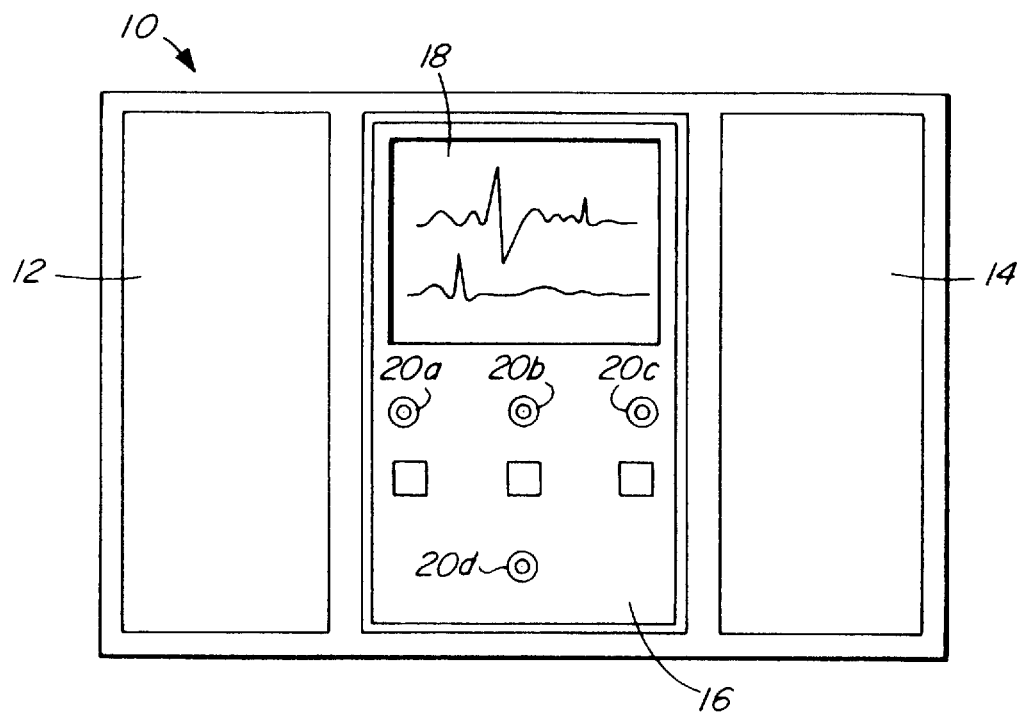
FIG. 1 is a general view of a cardiac display monitor incorporating the present invention.
Figure 2:
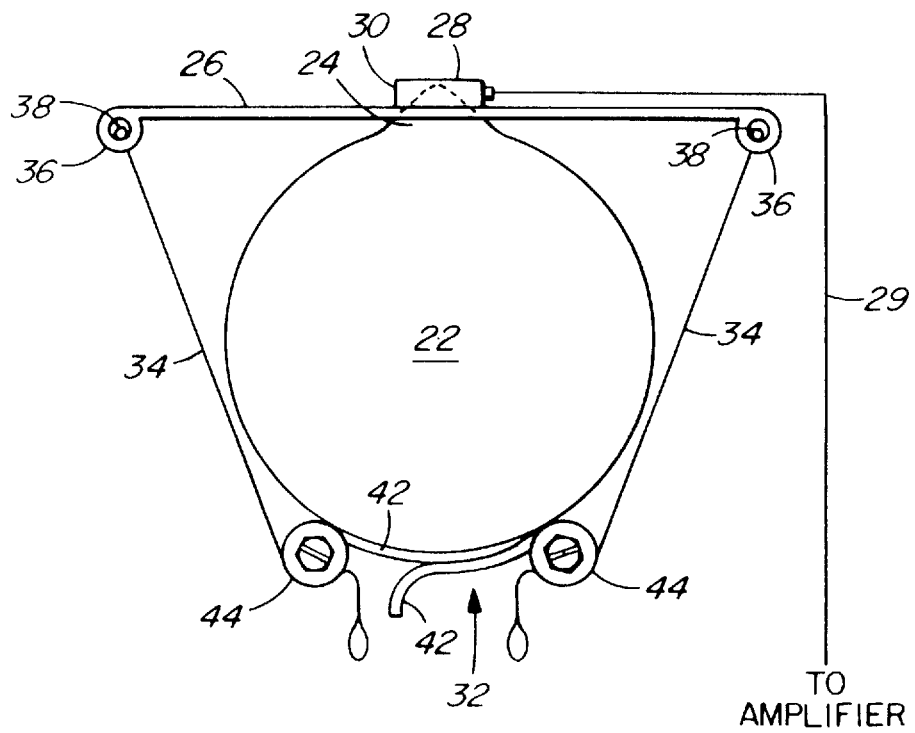
FIG. 2 is a plan view of the apparatus according to the present invention in position on a human wearer.

FIG. 1 shows a storage case 10 having compartments that can be used to store apparatus that will interpret and display signals from the apparatus of FIG. 2. The apparatus includes a compartment 12 for the storage of an accelerometer, a compartment 14 to hold ECG leads and a central compartment 16 to hold the cardiac display monitor having a display screen 18 and various switches 20a, 20b, 20c and 20d to enable switching between the various modes of operation of the apparatus according to the present invention.

Figure 2A:
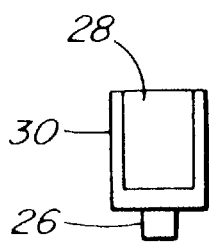
FIG. 2a is a cross-section through the accelerometer and supporting structure.

FIG. 2 shows the apparatus in place on a wearer. The wearer's neck 22 and thyroid cartilage 24 attached to the trachea, are shown. FIG. 2 shows a mounting strut 26 to extend across the front of the neck 22. There is an accelerometer 28 mounted on the strut 26 over the thyroid cartilage 24. As best shown in FIG. 2a, the strut 26 is provided with a central housing 30 that receives the accelerometer 28. The accelerometer may be glued in place. A co-axial cable 29 extends from it.

There is a releasible mount 32 to contact the back of the neck 22. Elastic members 34 extend between the mounting strut 26 and the releasible mount 32 to hold the apparatus in place. As shown in FIG. 2 the elastic members 34 do not contact the sides of the neck.

Figure 2B:
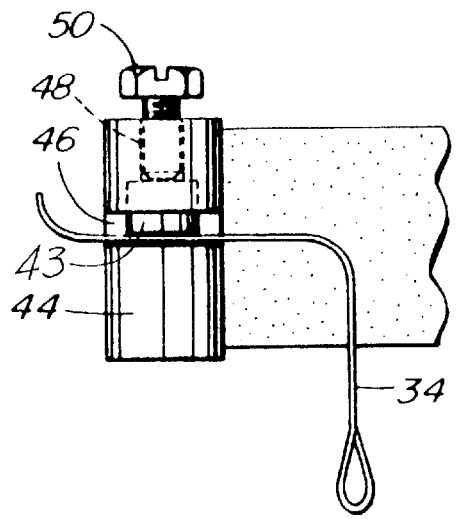
FIG. 2b illustrates a frictional clamp useful in the apparatus of FIG. 2.
Figure 2C:
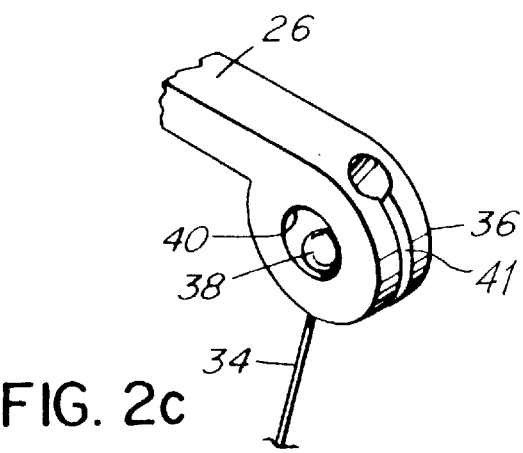
FIG. 2c illustrates a detail of the present invention.

The elastic members engage the struts at housings 36, one at each end of strut 26. As shown in FIG. 2c each member 34 has a bead 38, for example of copper, at its end. This bead 38 engages a recess 40 in housing 36. The member 34 fits in a slit 41 in the housing 36.

Releasable mount 32 comprises two straps 42 that can be releasably engaged, for example they can be hook and eye fastener strips. As best shown in FIG. 2b, each strap 42 has a clamp 44 at one end. Clamp 44 has a lateral passageway 46, a longitudinal passageway 48 and is internally threaded (not shown). Screw 50 is received in passageway 48 and acts to clamp and release a member 43 as it is rotated.

Figure 4:
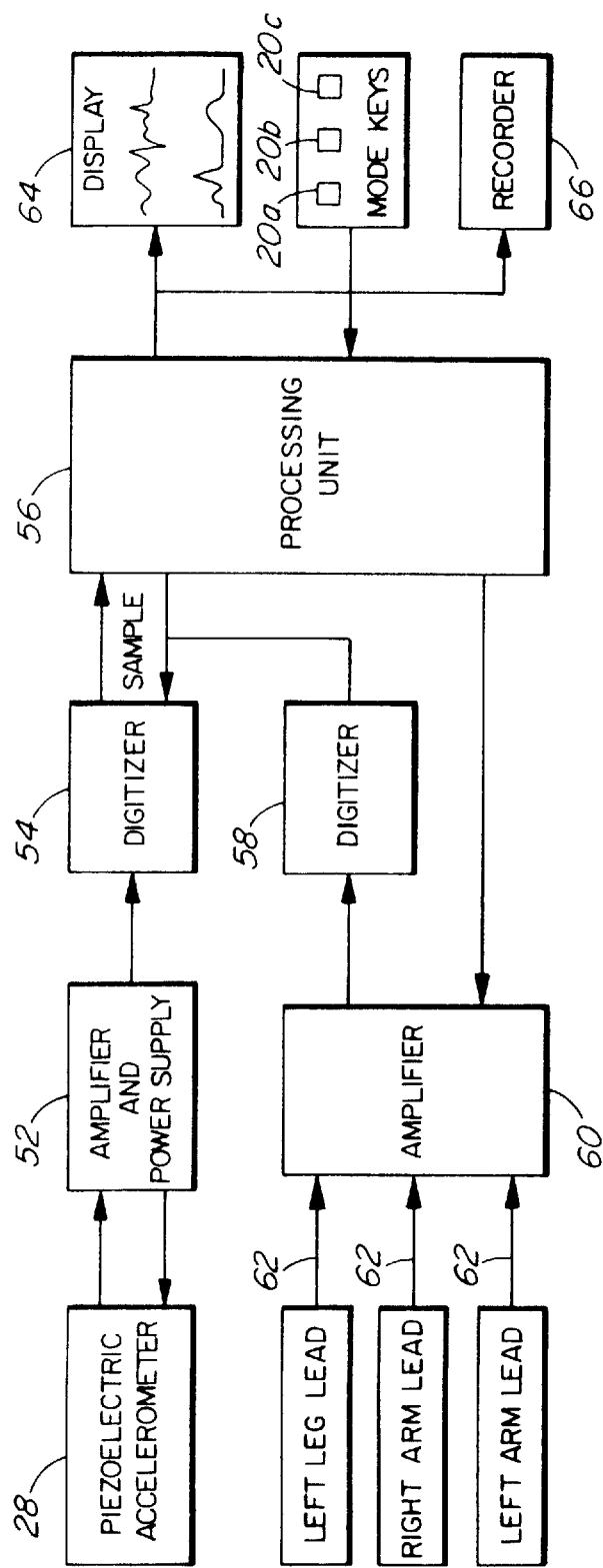
FIG. 4 is a schematic showing the heart monitoring circuitry.

Circuitry to enable operation of the device, in particular to produce a waveform characteristic of cardiac function, is illustrated in FIG. 4. FIG. 4 shows the accelerometer 28 in its preferred embodiment of a piezoelectric accelerometer. There is an amplifier and power supply 52 (which may be separate) that receives signals from, and sends power to, the accelerometer 28. The signal from the amplifier is fed to a digitizer 54 and the digitizer signal is fed to a processing unit 56. The processing unit 56 returns a signal to digitizer 54 and also sends a signal to a second digitizer 58.

The processing unit 56 also sends signals to a second amplifier 60 which, in turn, receives signals from leads 62, for example to the leg, right arm and left arm of the patient.

The processing unit 56 develops a signal which is sent to a display 64. If necessary the signal to the display 64 may be intercepted and forwarded to a recorder 66. There are mode keys, as also shown in FIG. 1, 20a, 20b and 20c.

The processing unit 56 produces two basic modes of output for the display 64. The signals are generated by the input from the piezoelectric accelerometer 28 and the electrocardium leads 62.

The first mode of display is simultaneous graphical display of two signals in waveform or trace. These signals are obtained from the input transducers and are the acceleration waveform received from the input piezoelectric accelerometer and the electrocardiogram waveform input from the leads. These waveforms are displayed with an amplitude represented on the vertical axis. The time is on the horizontal axis. The waveforms are displayed synchronized, (as shown diagrammatically in FIG. 4), such that at any particular time the values of each waveform will appear in the same vertical column on the display. Typically one or two heart beats will be present on the display.

The second mode of output displays a set of numbers calculated from the two input signals. Typically they will display:

(a) Heart rate
(b) Amplitude of maximum ejection rate
(c) Time interval of maximum ejection
(d) Amplitude of upper aortic volume change rate
(e) Amplitude of semi-lunar valve accelerate
(f) Total time interval for ventricular systolic
(g) Time interval from R-wave of E.C.G. to beginning of maximum ejection rate
(h) Time interval from R-wave of E.C.G. to closure of aortic valve
(i) % Heart attack risk.

These numbers would typically be presented in a textual formal and would be periodically calculated so as to reflect changes in heart function. The periodicity would, for example, be every heart beat or two.

Depending on the capability of the output display device used, both display modes may be present at the same time on the display, or the operator can depress button 20a to switch from one display mode to the other. The processing unit can automatically switch one display mode to the other every few seconds without operator intervention. Button 20b enables the processing unit 56 to eliminate the higher frequencies received and include only the acceleration of the thyroid cartilage as a result of respiration. Button 20c eliminates the respiratory low frequency events and thus provides a more stable baseline to record the cardiovascular events.

The processing unit continually accepts inputs from the amplified and periodically digitized accelerometer transducer and the amplitude and periodically digitized E.C.G. signals. The processing unit 56 controls the gain of these signal amplifiers so that usable waveform information is input to the processing unit 56 for the waveform unit for the wave form or trace display in the first display.

The information presented in the second mode display is a permanent record and may be retained using a recorder. In recording the dynamic heart forces the breath may be held at various phases of the breathing cycle and recordings made. This provide a valuable diagnostic aid. Records may also be obtained after hyperventilation of ambient air. Subsequently comparative records can be obtained with hyperventilation of air containing a known decrease in oxygen and increase in carbon dioxide. These comparisons can provide valuable information about physiological condition of a pulmonary and cardiac system.

Records obtained during large negative abdominal pressures as a result of forced inspiration with the nose pinched and the mouth closed cause a normal heart and lung to increase the amplitude of the maximum ejection rate and aortic valve acceleration. If high pulmonary resistance exists there will be little change in the amplitude from records taken with the nose and mouth open.

An appropriate piezoelectric accelerometer is one having a frequency response of 0.1 Hz to 700 Hz, a sensitivity (acceleration) of 50 mV/M/S$^2$, a resolution of 0.002 M/S$^2$, a power (constant current) of about 12 volts D.C. and 1 mA and a weight of about 3 grams.

The strut 26 should be light weight and is, for example, of aluminum. Strut 26 is desirably coated with a material having high co-efficient of friction and should have poor thermal conductivity.

Figure 3:
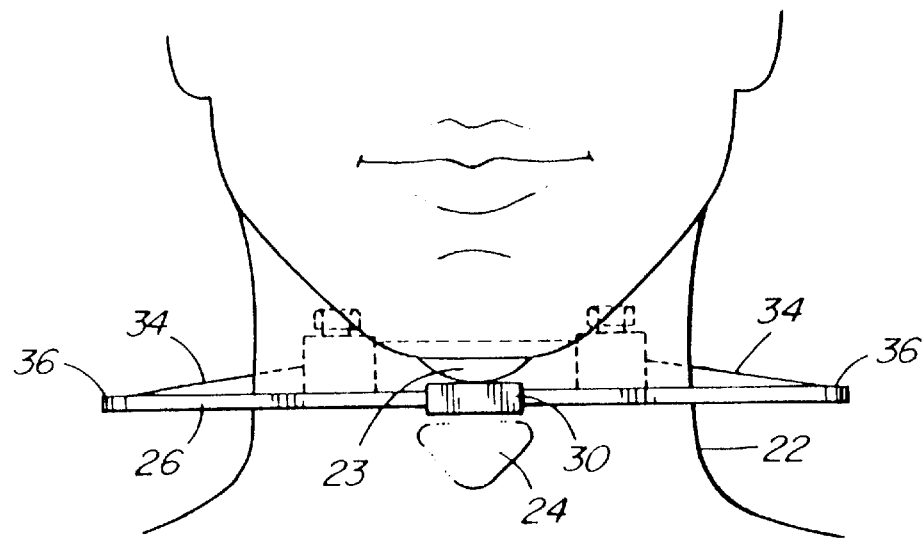
FIG. 3 illustrates the positioning of the apparatus against the thyroid cartilage.

To use the device according to the invention the accelerometer, contained in the housing 30, is placed on the thyroid cartilage, as shown particularly in FIG. 3, against the trachea and beneath the soft tissue 23 of the jaw. The housing 30 abuts the top or horizontal surface of the cartilage 24. Co-axial cable 29 extending from the accelerometer 28 is desirably glued onto the strut 26. The beads 38 of the elastic members 34 are inserted through the housings 36 at the end of each strut 26 and pulled through slit 40 in the wall of the housing. The elastic members 34 are then pulled into and through the lateral passageways 46 of the clamps 44 located on the clamping means 32. Screws 50 are tightened to locate the elastic members 34 in place. The elastic members 34 do not contact the neck at any point and are evenly positioned on either side of the neck 22. They are not so tensioned as to cause discomfort. This positioning allows placement of the accelerometer 28 in an appropriate position on the thyroid cartilage 24 while retaining good contact with the trachea and the thyroid cartilage. The elastic members are desirably of small diameter so as not to produce any torque that would tend to move the accelerometer away from the thyroid cartilage.

During the taking of measurements it is preferable to have the patient seated. However if the subject has a large abdomen a standing position may be preferred. If a prone position is required, a pillow of sufficient height is provided to bend the head towards the chest. This bending is also essential in the sitting and standing position in order to free the trachea with the attached thyroid, to move easily, longitudinally of the body axis, in response to the acceleration and deceleration forces generated by cardiac mass motion and blood ejection. Unless the head is bent towards the chest no useful record can be obtained. The movement also secures the apparatus in place by clamping it between the cartilage, the trachea and the soft tissue of the jaw—see FIG. 3.

It is possible, for example in the case of athletes to leave the apparatus positioned on the thyroid cartilage during exercise so that periodic examination of the display can take place quickly during exercise.

To discuss the results achieved, in the interest of brevity, only the events of ventricular systoli will be analyzed; presystolic events will be discounted. Further, for brevity, records obtained from patients with a variety of other cardiovascular abnormalities are omitted. Sufficient examples of abnormal heart function will be illustrated to show the value of this method and apparatus in diagnosis. Traces obtained of heart forces are precise and repeatable.

Figure 5:
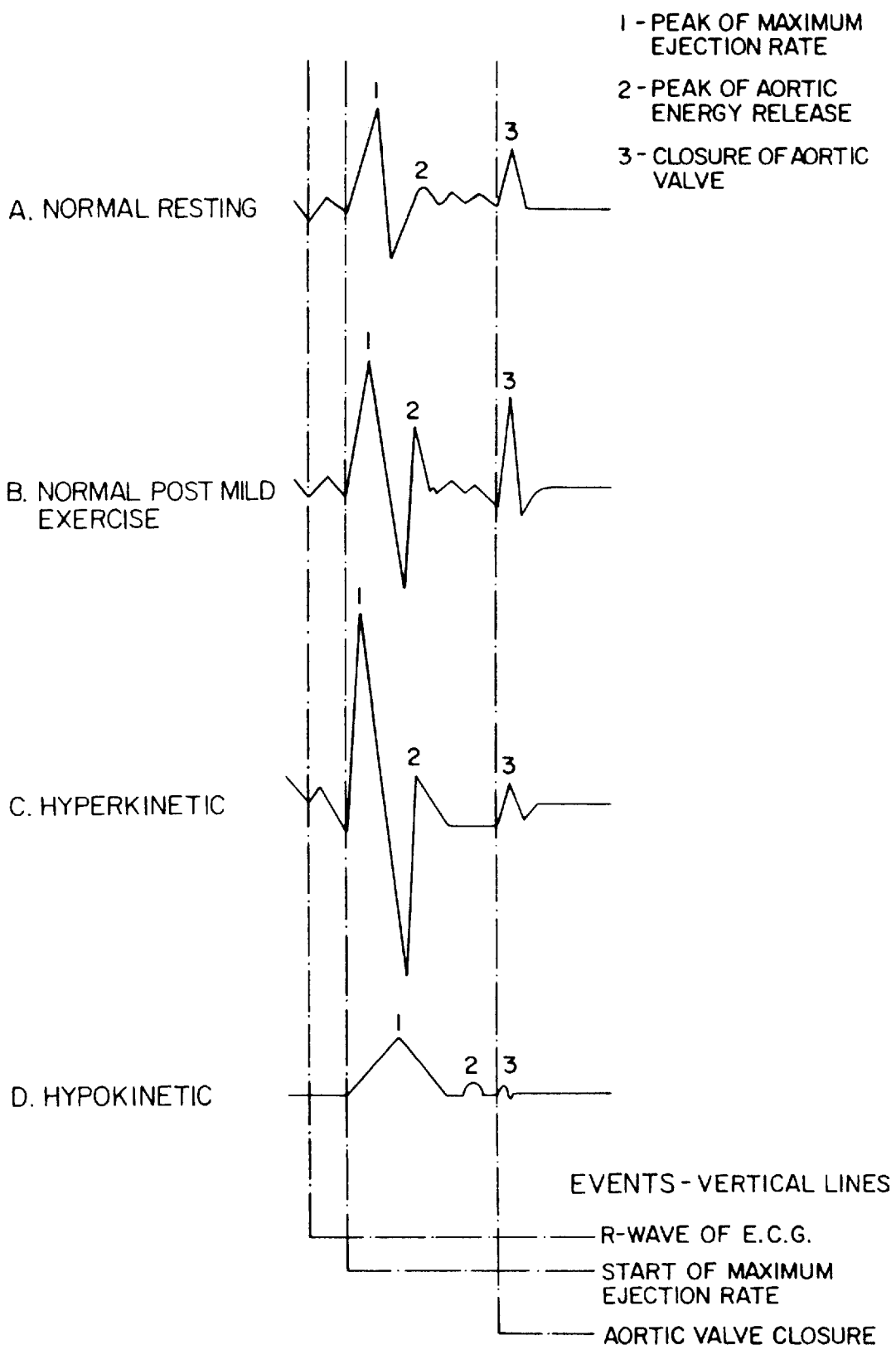
FIG. 5 shows various waveforms typical of normal and abnormal hearts.

These results are illustrated in FIG. 5, lines A to D. This Figure shows typical traces with a vertical line at the beginning of the accelerator curve of maximum ventricular ejection in order to best compare variation of pattern from the normal trace. The amplitude of the traces is displayed vertically while time is displayed horizontally. Each peak has a main wave as follows. Wave 1 shows a maximum ventricular ejection rate; wave 2 shows the upper aortic volume change rate and wave 3 shows a semi-lunar valve acceleration.

FIG. 5, line A shows a normal heart. The amplitudes and time intervals are sampled for the general population. The means and standard deviation is determined. Patient values are then compared. The Z value is determined for the amplitude and time intervals. Any z value greater than one is considered abnormal. If a trace after a stress test increases in amplitude as shown in trace of FIG. 5b, without any basic deviation of the normal pattern shown in 5, line A then the heart is normal in function. However the pattern changes dramatically, with a complete breakdown of periodicity and decrease in wave amplitude, then there exists a serious decrease of heart function.

The invention permits the determination of a heart attack risk. Heart attack risk ratio is determined by maximum ejection amplitude in millimeters by the maximum ejection time interval in milliseconds. The mean and standard deviation is then determined from a random sample of the population. The patient's heart attack ratio is also determined and a Z score determined according to the equation:

$$Zi = \frac{Xi - X}{S.T.D.}$$

where S.T.D. is standard deviation.

The risk of heart attack is determined from the following table:

| Z score | % Heart Attack Risk |
| --- | --- |
| 1 | 25% |
| 2 | 50% |
| 3 | 75% |
| 4 | 100% |

Other waveform processing can be obtained using easily available software programs. The programs consist of such mathematical techniques as differentiation, integration, signal averaging and signal comparison. To distinguish normal pathological waveform further differentiation of the acceleration waveforms can provide a clear difference.

Although the present invention has been described in some detail by way of illustration and example for purposes of clarity and understanding, it will be readily apparent to those of ordinary skill in the art in light of the teachings of this invention that certain changes and modifications may be made thereto without departing from the spirit or scope of the appended claims.

I claim:

1. Apparatus to assess cardiac function in a human that comprises:

sensing means to be positioned on the thyroid cartilage in the neck, against the trachea and able to sense the response of the thyroid cartilage to heart function and generate a signal indicative of the response of the thyroid cartilage;

means to retain the sensing means in said position; and a signal processing unit to receive the signal from the sensing means and generate a waveform signal characteristic of the heart function for assessment by a user.

2. Apparatus as claimed in claim 1 in which the sensing means is an accelerometer.

3. Apparatus as claimed in claim 1 in which the sensing means is adapted to sense the response of the thyroid cartilage by detecting the displacement thereof.

4. Apparatus as claimed in claim 3 in which the sensing means is adapted to sense the response of the thyroid cartilage by detecting the acceleration or velocity thereof.

5. Apparatus to assess cardiac function in a human, the apparatus comprising:

a mounting strut to extend across the front of the neck of the human;

an accelerometer mounted on said strut to be positionable over the thyroid cartilage in said neck to detect the response of said thyroid cartilage to heart function and generate a signal indicative of said response;

mounting means to retain said accelerometer on said neck; and a signal processing unit to receive the signal from the accelerometer and generate a waveform signal characteristic of the heart function of assessment by a user.

6. Apparatus as claimed in claim 5 in which the mounting strut has a central housing to receive the accelerometer.

7. Apparatus as claimed in claim 5 in which the mounting strut has a housing, proximate each end, to receive said mounting means.

8. Apparatus as claimed in claim 7 in which the mounting means are elastic.

9. Apparatus as claimed in claim 8 in which the mounting means comprise an elastic member extending from each of the housings on said mounting strut to fit around the neck of the wearer.

10. Apparatus as claimed in claim 9 in which the mounting means include strap members to contact the back of said neck, the strap members including fastening means to permit releasable attachment to each other.

11. Apparatus as claimed in claim 10 in which there is a clamp at the end of each strap member to hold the elastic members.

12. Apparatus as claimed in claim 11 in which each clamp comprises:

a housing having a lateral passageway to receive one of the elastic members;

an internally threaded, longitudinal passageway;

a compressing screw to engage said longitudinal passageway and to compress the elastic member in the lateral passageway to hold the elastic member in place.

13. Apparatus as claimed in claim 10 in which the fastening means comprises a hook and eye fastener.

14. Apparatus as claimed in claim 9 in which each elastic member has a bead;

each housing having an opening and a slot;

each elastic member fitting in a corresponding one of the slots and the bead in a corresponding one of the openings of the housings to retain the elastic member in the housing.

15. Apparatus as claimed in claim 5 in which the accelerometer is a piezoelectric accelerometer.

16. Apparatus as claimed in claim 5 in which the signal processing unit includes;

a power source for the accelerometer;

an amplifier to amplify the signal from the accelerometer;

a digitizer to digitize the amplified signal;

a signal analysis unit to analyze the amplified signal and generate the waveform signal characteristic of the heart function; and means to provide a display of the waveform signal.

17. Apparatus as claimed in claim 16 in which there is a recorder to record the waveform signal from the processing unit.

18. A method of determining cardiac function that comprises the steps of:

sensing the response of the thyroid and trachea to heart function;

generating and displaying a waveform signal based on the response of the thyroid and trachea; and assessing the waveform signal to determine the heart function.

19. A method of determining cardiac function comprising the steps of:

locating sensing means on the neck of a patient at the patient's thyroid cartilage and against the trachea sensing the response of the thyroid cartilage and trachea to heart function with the sensing means generating a signal indicative of said response;

processing the signal to generate a displayed waveform signal characteristic of the heart function; and assessing the waveform signal to determine the heart function.

20. A method as claimed in claim 19 in which the sensing step comprises detecting the response of the thyroid cartilage and trachea by measuring the acceleration, velocity or displacement of the thyroid cartilage and trachea.

* * * * *